(12) United States Patent
Yang et al.

(10) Patent No.: US 10,539,491 B2
(45) Date of Patent: Jan. 21, 2020

(54) APPARATUS AND METHOD FOR MEASURING ERYTHROCYTE SEDIMENTATION RATE

(71) Applicant: GWANGJU INSTITUTE OF SCIENCE AND TECHNOLOGY, Gwangju (KR)

(72) Inventors: Sung Yang, Gwangju (KR); Alexander Zhbanov, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 16/502,660

(22) Filed: Jul. 3, 2019

(65) Prior Publication Data

US 2019/0323984 A1   Oct. 24, 2019

Related U.S. Application Data

(62) Division of application No. 15/349,019, filed on Nov. 11, 2016.

(30) Foreign Application Priority Data

Nov. 12, 2015  (KR) .................. 10-2015-0159141

(51) Int. Cl.
*G01N 15/05* (2006.01)
*G01N 27/327* (2006.01)
*G01N 33/49* (2006.01)
*G01N 33/487* (2006.01)

(52) U.S. Cl.
CPC ......... *G01N 15/05* (2013.01); *G01N 27/3275* (2013.01); *G01N 33/48707* (2013.01); *G01N 33/49* (2013.01); *G01N 33/491* (2013.01)

(58) Field of Classification Search
CPC ........ G01N 27/3275; G01N 33/48707; G01N 33/49; G01N 33/491
USPC .............................. 436/70; 422/73, 560, 561
See application file for complete search history.

(56) References Cited

U.S. PATENT DOCUMENTS

2015/0253269 A1    9/2015  Katsumoto

OTHER PUBLICATIONS

Zhbanov et al., Effect of Erythrocyte Sedimentation and Aggregation on the Conductivity of Blood in a Miniature Chamber, ICQNM 2012 : The Sixth International Conference on Quantum, Nano and Micro Technologies (ISBN: 978-1-61208-214-1) (Year: 2012).*

(Continued)

*Primary Examiner* — Dean Kwak
(74) *Attorney, Agent, or Firm* — Hauptman Ham, LLP

(57) ABSTRACT

An apparatus and method for measuring an erythrocyte sedimentation rate based on a change in conductivity of blood over time. The apparatus for measuring an erythrocyte sedimentation rate may include: a chamber for holding blood; a pair of electrodes being partially or completely brought into contact with the blood; and a conductivity meter measuring the conductivity through the pair of electrodes. The apparatus and method according to the present invention are less time-consuming than the Westergren method and can acquire a variety of information (for example, hematocrit, dynamics of the sedimentation rate and aggregation of erythrocytes, a relationship between the sedimentation rate and aggregation of erythrocytes, and the like).

8 Claims, 3 Drawing Sheets

(56) References Cited

OTHER PUBLICATIONS

Alexy et al., A rapid method to estimate Westergren sedimentation rates, Review of Scientific Instruments 80, 096102 (2009) (Year: 2009).*
Alexander Zhbanov et al., "An alternative, rapid method to evaluation of erythrocyte sedimentation rate", Gwangju Institute of Science and Technology, May 25, 2015, total 1 page.
Alexander Zhbanov et al., "Effects of Aggregation on Blood Sedimentation and Conductivity", PLOS One, Jun. 5, 2015, total 25 pages.
Kichul Cha et al., "A new bioelectrical impedance method for measurement of the erythrocyte sedimentation rate", Physiol Meas, 1994, p. 499-508, 15, total 11 pages.
A. Pribush et al. "The mechanism of erythrocyte sedimentation. Part 1: Channeling in sedimenting blood", Colloids and Surf B—Biointerfaces, 2010, p. 214-223, 75, total 10 pages.
A. Pribush et al., "The mechanism of erythrocyte sedimentation. Part 2: The global collapse of settling erythrocyte network", Colloids and Surf B—Biointerfaces, 2010, p. 224-229, 75, total 6 pages.
Alexander Pribush et al., "The effect of the prior flow velocity on the structural organization of aggregated erythrocytes in the quiescent blood", Colloids and Surf B—Biointerfaces, 2011, p. 518-525, 82, total 8 pages.
A. Pribush et al., "A novel approach for assessments of erythrocyte sedimentation rate", International Journal of Laboratory Hematology, 2011, p. 251-257, 33, total 7 pages.
Byung Jun Kim et al., Measurement of Red Blood Cell Aggregation and Sedimentation Rate Using Bottom and Wall-Patterned Electrodes, DBpia, Dec. 2013, pp. 3850-3851, The Korean Society of Mechanical Engineers.
Korean Office Action dated Sep. 27, 2016 in connection with the counterpart Korean Patent Application No. 10-2015-0159141.

* cited by examiner

APPARATUS AND METHOD FOR MEASURING ERYTHROCYTE SEDIMENTATION RATE

CROSS REFERENCE TO RELATED APPLICATION

This application is a Divisional Application of U.S. application Ser. No. 15/349,019 filed Nov. 11, 2016 which claims the benefit of Korean Patent Application No. 10-2015-0159141, filed on Nov. 12, 2015, entitled "APPARATUS AND METHOD FOR MEASURING ERYTHROCYTE SEDIMENTATION RATE", which is hereby incorporated by reference in its entirety into this application.

BACKGROUND

1. Technical Field

The present invention relates to an apparatus and method for measuring an erythrocyte sedimentation rate, and, more particularly, to an apparatus and method for measuring an erythrocyte sedimentation rate based on conductivity of blood measured by a pair of electrodes.

2. Description of the Related Art

Determination of an erythrocyte sedimentation rate (ESR) is a useful blood test capable of providing an index of inflammation or an acute phase reaction of a patient. The ESR test was invented in 1897 by a Polish physician, Edmund Faustyn Biernacki. Similar methods were reported in 1918 by Robert Sanno Fahraeus and in 1921 by Alf Vilhelm Westergren. Particularly, Westergren's method spread quickly all over the world due to simplicity and low cost thereof.

In the Westergren test, venous blood is mixed with sodium citrate in a ratio of 4:1 and then collected in a glass or plastic tube having a minimum sedimentation scale of 200 mm and a minimum bore of 2.55 mm. The tube is placed on a Westergren stand in a vertical position at room temperature for 1 hour. Then, a distance from the lowest point of a surface meniscus to an uppermost layer of an erythrocyte sediment is measured. The distance of fall of erythrocytes, expressed as millimeters per hour (mm/h), is recorded as the ESR.

Since the Westergren test takes 1 hour, which is much longer than the time required for general automated blood tests, a method for measuring an ESR in a shorter period of time is being studied by many research groups.

There has been proposed a method of measuring electrical impedance of blood columns to find an ESR. Resistance of blood is closely related with hematocrit (HCT). A simple equation for finding an ESR using plasma resistance, membrane capacitance, and HCT may be obtained by linear regression. In addition, time-dependence of the ESR and conductivity has been examined by Cha et al. [1] and Pribush et al. [2-5].

[1] Cha K, Brown E F, Wilmore D W. A new bioelectrical impedance method for measurement of the erythrocyte sedimentation rate. Physiol Meas. 1994; 15: 499-508.

[2] Pribush A, Meyerstein D, Meyerstein N. The mechanism of erythrocyte sedimentation. Part 1: Channeling in sedimenting blood. Colloid Surf B-Biointerfaces. 2010; 75: 214-223.

[3] Pribush A, Meyerstein D, Meyerstein N. The mechanism of erythrocyte sedimentation. Part 2: The global collapse of settling erythrocyte network. Colloid Surf B-Biointerfaces. 2010; 75: 224-229.

[4] Pribush A, Meyerstein D, Meyerstein N. The effect of the prior flow velocity on the structural organization of aggregated erythrocytes in the quiescent blood. Colloid Surf B-Biointerfaces. 2011; 82: 518-525.

[5] Pribush A, Hatskelzon L, Meyerstein N. A novel approach for assessments of erythrocyte sedimentation rate. Int J Lab Hematol. 2011; 33: 251-257.

Such researches focus on the phenomenon that, as erythrocytes settle over time, the HCT decreases at an upper portion of a blood column.

In these methods, electrodes are placed at an upper portion of a blood column, followed by measuring an ESR based on electrical impedance. However, these methods have a problem in that the erythrocyte aggregation reduces the sensitivity over time, and thus it is impossible to accurately measure the erythrocyte sedimentation rate.

BRIEF SUMMARY

It is an aspect of the present invention to provide an apparatus and method for measuring an erythrocyte sedimentation rate, which is less time-consuming than the Westergren method and can acquire a variety of information (for example, hematocrit, dynamics of the sedimentation rate and aggregation of erythrocytes, a relationship between the sedimentation rate and aggregation of erythrocytes, and the like).

In accordance with one aspect of the present invention, there is provided an apparatus for measuring an erythrocyte sedimentation rate based on a change in conductivity of blood over time.

The apparatus for measuring an erythrocyte sedimentation rate may include: a chamber for holding blood; a pair of electrodes being partially or completely brought into contact with the blood; and a conductivity meter measuring the conductivity through the pair of electrodes.

The pair of electrodes may be placed on a bottom surface of the chamber.

The change in conductivity may be found based on a difference between conductivities measured at two points of time.

The two points of time may be selected from a time section after the conductivity starts to decrease.

The erythrocyte sedimentation rate may be measured through comparison of the change in conductivity with an erythrocyte sedimentation rate measured by the Westergren method.

A relationship between the change in conductivity and the erythrocyte sedimentation rate measured by the Westergren method may be represented by the following equation:

$$\Delta\sigma = \lambda W^\gamma$$

where $\Delta\sigma$ denotes a difference (unit: S/m) between blood conductivities measured at predetermined points of time, W denotes an erythrocyte sedimentation rate (unit: mm/h) measured by the Westergren method, and $\lambda$ and $\gamma$ denote fitting parameters, wherein the fitting parameters may be calculated by regression analysis.

The predetermined points of time may be 200 seconds and 400 seconds, respectively, and $\Delta\sigma$ may be calculated by $\sigma_{200} - \sigma_{400}$, wherein $\sigma_{200}$ denotes a conductivity measured when 200 seconds elapse after erythrocytes start to settle, and $\sigma_{400}$ denotes a conductivity measured when 400 seconds elapse after erythrocytes start to settle.

The conductivity meter may measure impedance between the pair of electrodes to find the conductivity.

A relationship between the change in conductivity and the erythrocyte sedimentation rate measured by the Westergren method may be represented by the following equation:

$$\Delta\sigma = \lambda \log(1+W)$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ denotes fitting parameters, wherein the fitting parameters may be calculated by regression analysis.

A relationship between the change in conductivity and the erythrocyte sedimentation rate measured by the Westergren method may be represented by the following equation:

$$\Delta\sigma = \lambda \frac{W}{W+\gamma}$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ and $\gamma$ denote fitting parameters, wherein the fitting parameters may be calculated by regression analysis.

A relationship between the change in conductivity and the erythrocyte sedimentation rate measured by the Westergren method may be represented by the following equation:

$$\Delta\sigma = \lambda\left[\left(\frac{1}{\gamma}\right)^2 - \left(\frac{1}{W+\gamma}\right)^2\right]$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ and $\gamma$ denote fitting parameters, wherein the fitting parameters may be calculated by regression analysis.

In accordance with another aspect of the present invention, there is provided a method for measuring an erythrocyte sedimentation rate based on a change in conductivity of blood over time.

The method for measuring an erythrocyte sedimentation rate may include: introducing blood into a chamber; and measuring conductivity of the blood using a pair of electrodes.

The pair of electrodes may be placed in a bottom surface of the chamber.

The change in conductivity may be found based on a difference between conductivities measured at two points of time.

The two points of time may be selected from a time section after the conductivity starts to decrease.

The erythrocyte sedimentation rate may be measured through comparison of the change in conductivity with an erythrocyte sedimentation rate measured by the Westergren method.

A relationship between the change in conductivity and the erythrocyte sedimentation rate measured by the Westergren method may be represented by the following equation:

$$\Delta\sigma = \lambda W^{\gamma}$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ and $\gamma$ denote fitting parameters, wherein the fitting parameters may be calculated by regression analysis.

A relationship between the change in conductivity and the erythrocyte sedimentation rate measured by the Westergren method may be represented by the following equation:

$$\Delta\sigma = \lambda \log(1+W)$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ denotes fitting parameters, wherein the fitting parameters may be calculated by regression analysis.

A relationship between the change in conductivity and the erythrocyte sedimentation rate measured by the Westergren method may be represented by the following equation:

$$\Delta\sigma = \lambda \frac{W}{W+\gamma}$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ and $\gamma$ denote fitting parameters, wherein the fitting parameters may be calculated by regression analysis.

A relationship between the change in conductivity and the erythrocyte sedimentation rate measured by the Westergren method may be represented by the following equation:

$$\Delta\sigma = \lambda\left[\left(\frac{1}{\gamma}\right)^2 - \left(\frac{1}{W+\gamma}\right)^2\right]$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ and $\gamma$ denote fitting parameters, wherein the fitting parameters may be calculated by regression analysis.

According to the present invention, it is possible to provide an apparatus and method for measuring an erythrocyte sedimentation rate, which can measure the erythrocyte sedimentation rate within 400 seconds, which is shorter than the about 1 hour required in the Westergren method, and can easily measure and acquire a variety of information such as hematocrit, dynamics of the sedimentation rate and aggregation of erythrocytes, a relationship between the sedimentation rate and aggregation of erythrocytes, and the like.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Hereafter, an apparatus and method for measuring an erythrocyte sedimentation rate will be described with reference to the accompanying drawings. The above and other aspects, features, and advantages of the present invention will become apparent to those skilled in the art from the detailed description of the following embodiments in conjunction with the accompanying drawings.

As used herein, the term "exemplary" is used to mean serving as an "example, instance, or illustration". Here, any "exemplary" embodiment or aspect should not be construed as preferred or advantageous over other embodiments or aspects.

As used herein, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Although the terms first, second, etc. may be used herein to describe various elements, components, regions, layers, and/or sections, these elements, components, regions, layers, and/or sections should not be limited by these terms.

As used herein, the singular forms, "a," "an," and "the" are intended to include the plural forms as well, unless context clearly indicates otherwise.

Figure 1:
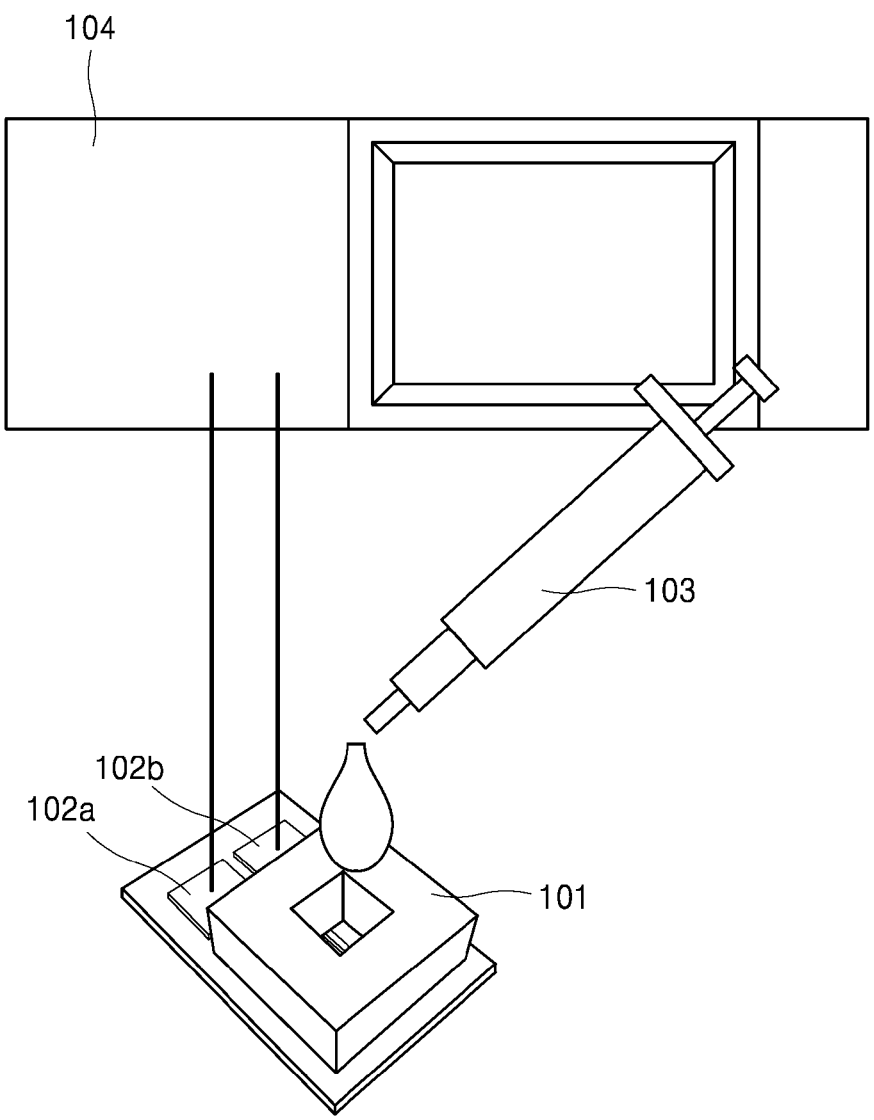
FIG. 1 is a view of an apparatus for measuring an erythrocyte sedimentation rate according to one embodiment of the present invention.

FIG. 1 is a view of an apparatus for measuring an erythrocyte sedimentation rate according to one embodiment of the present invention.

Referring to FIG. 1, the apparatus for measuring an erythrocyte sedimentation rate according to this embodiment of the present invention may include: a chamber 101 for holding blood; a pair of electrodes 102a, 102b for measuring conductivity; a blood injector 103; and a conductivity meter 104.

Blood is introduced into the chamber 101 using the blood injector 103; the pair of electrodes 102a, 102b is partially brought into contact with the blood in the chamber 101; and the conductivity meter 104 may measure conductivity between the pair of electrodes 102a, 102b.

For example, the conductivity meter 104 may be an impedance analyzer which analyzes resistance between the pair of electrodes 102a, 102b, thereby finding the conductivity.

According to an exemplary embodiment of the invention, the pair of electrodes 102a, 102b may be placed on a bottom surface of the chamber 101. If the electrodes are placed at an upper portion of the chamber 101, it is impossible to accurately measure change in conductivity caused by sedimentation of erythrocytes toward a bottom of the chamber 101 over time.

Once the conductivity is measured by the conductivity meter 104, it is possible to measure an erythrocyte sedimentation rate through comparison of the conductivity with an erythrocyte sedimentation rate measured by the Westergren method.

A relationship between the conductivity and the erythrocyte sedimentation rate measured by the Westergren method may be represented by Equations 1 to 4:

$$\Delta\sigma = \lambda W^{\gamma} \qquad \text{<Equation 1>}$$

where $\Delta\sigma$ denotes a difference (unit: S/m) between conductivities of blood measured at predetermined points of time, W denotes an erythrocyte sedimentation rate (unit: mm/h) measured by the Westergren method, $\lambda$ and $\gamma$ denote fitting parameters. The fitting parameters are calculated by regression analysis, and $\lambda$ and $\gamma$ have values of 0.02049 and 0.254 respectively, as calculated by an experimental method according to one embodiment of the present invention. By way of example, the regression analysis may be a least squares method.

$$\Delta\sigma = \lambda \log(1+W) \qquad \text{<Equation 2>}$$

where $\Delta\sigma$ denotes a difference (unit: S/m) between conductivities of blood measured at predetermined points of time; W denotes an erythrocyte sedimentation rate (unit: mm/h) measured by the Westergren method; and $\lambda$ denotes fitting parameters, wherein the fitting parameters are calculated by regression analysis, and $\lambda$ has a value of 0.0145, as calculated by an experimental method according to one embodiment of the present invention. By way of example, the regression analysis may be a least squares method.

$$\Delta\sigma = \lambda \frac{W}{W+\gamma} \qquad \text{<Equation 3>}$$

where $\Delta\sigma$ denotes a difference (unit: S/m) between conductivities of blood measured at predetermined points of time; W denotes an erythrocyte sedimentation rate (unit: mm/h) measured by the Westergren method; and $\lambda$ and $\gamma$ denote fitting parameters. The fitting parameters are calculated by regression analysis, and $\lambda$ and $\gamma$ have values of 0.085 and 25 respectively, as calculated by an experimental method according to one embodiment of the present invention. By way of example, the regression analysis may be a least squares method.

$$\Delta\sigma = \lambda\left[\left(\frac{1}{\gamma}\right)^2 - \left(\frac{1}{W+\gamma}\right)^2\right] \qquad \text{<Equation 4>}$$

where $\Delta\sigma$ denotes a difference (unit: S/m) between conductivities of blood measured at predetermined points of time; W denotes an erythrocyte sedimentation rate (unit: mm/h) measured by the Westergren method; and $\lambda$ and $\gamma$ denote fitting parameters. The fitting parameters are calculated by regression analysis, and $\lambda$ and $\gamma$ have values of 280 and 60 respectively, as calculated by an experimental method according to one embodiment of the present invention. By way of example, the regression analysis may be a least squares method.

Equations 1 to 4 have substantially the same plot in all possible ranges of W ($0 \leq W \leq 200$), when $\lambda$ has a value of 0.0145 and $\gamma$ has a value of 25.

Preferably, $\Delta\sigma$ is calculated by $\sigma_{200} - \sigma_{400}$. Here, $\sigma_{200}$ denotes a conductivity measured when 200 seconds elapse after erythrocytes start to settle, and $\sigma_{400}$ denotes a conductivity measured when 400 seconds elapse after erythrocytes start to settle.

Figure 2:
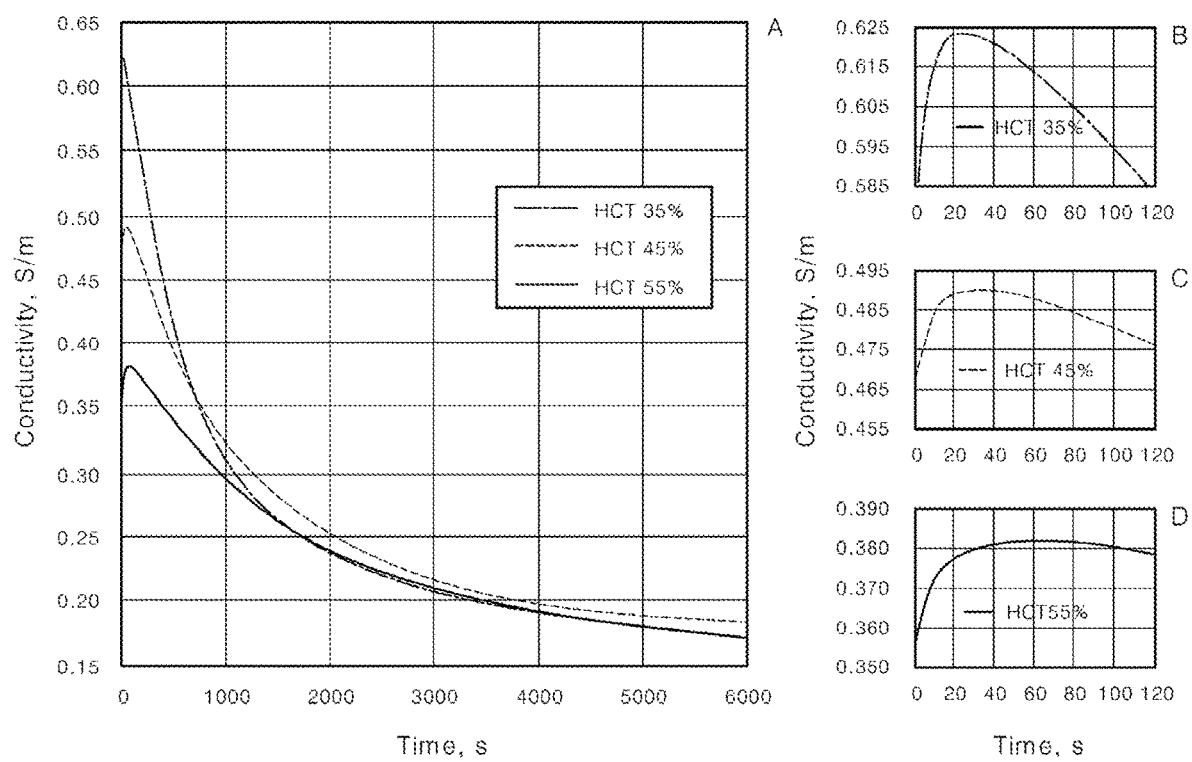
FIG. 2 is a graph showing conductivities measured on blood samples having different hematocrits (HCTs) after starting of erythrocyte sedimentation.

FIG. 2 is a graph showing conductivity measured in blood samples having different hematocrits (HCTs) after starting of erythrocyte sedimentation.

Specifically, FIG. 2 shows changes in conductivity over time, as measured at an HCT of 35%, 45%, and 55% after starting of erythrocyte sedimentation. FIG. 2(A) is a graph obtained by combining graphs plotted for three HCTs; and FIGS. 2(B), 2(C), and 2(D) are enlarged graphs showing changes in conductivity measured at respective HCTs before 120 seconds elapse.

Referring to FIGS. 2(B), 2(C), and 2(D), it can be seen that the conductivity at each HCT value increases at an early stage where erythrocytes start to settle. Thereafter, the conductivity at HCTs of 35%, 45%, and 55% reaches the maximum values after 18 seconds, 31 seconds, and 60 seconds, respectively, and then gradually decreases.

The reason that the conductivity increases at an early stage is because aggregation of erythrocytes has a greater influence on conductivity at the early stage. Aggregation of erythrocytes increases conductivity and erythrocyte sedimentation rate. More specifically, the reason the conductivity increases at an early stage (before 18 seconds elapse when HCT is 35%, before 31 seconds elapse when HCT is 45%, and before 60 seconds elapse when HCT is 55%) is because, at the early stage, the conductivity is more influenced by aggregation of erythrocytes than by sedimentation of erythrocytes which causes reduction in conductivity.

For this reason, according to the present invention, preferably, two points of time are selected in a time section where the conductivity starts to decrease, followed by comparing a difference between the conductivity measured at the two points of time with an erythrocyte sedimentation rate found by the Westergren method. More preferably, conductivities at a point of time of 200 seconds and 400 seconds are measured such that the erythrocyte sedimentation rate can be measured within 400 seconds while minimizing the influence of erythrocyte aggregation on conductivity.

Figure 3:
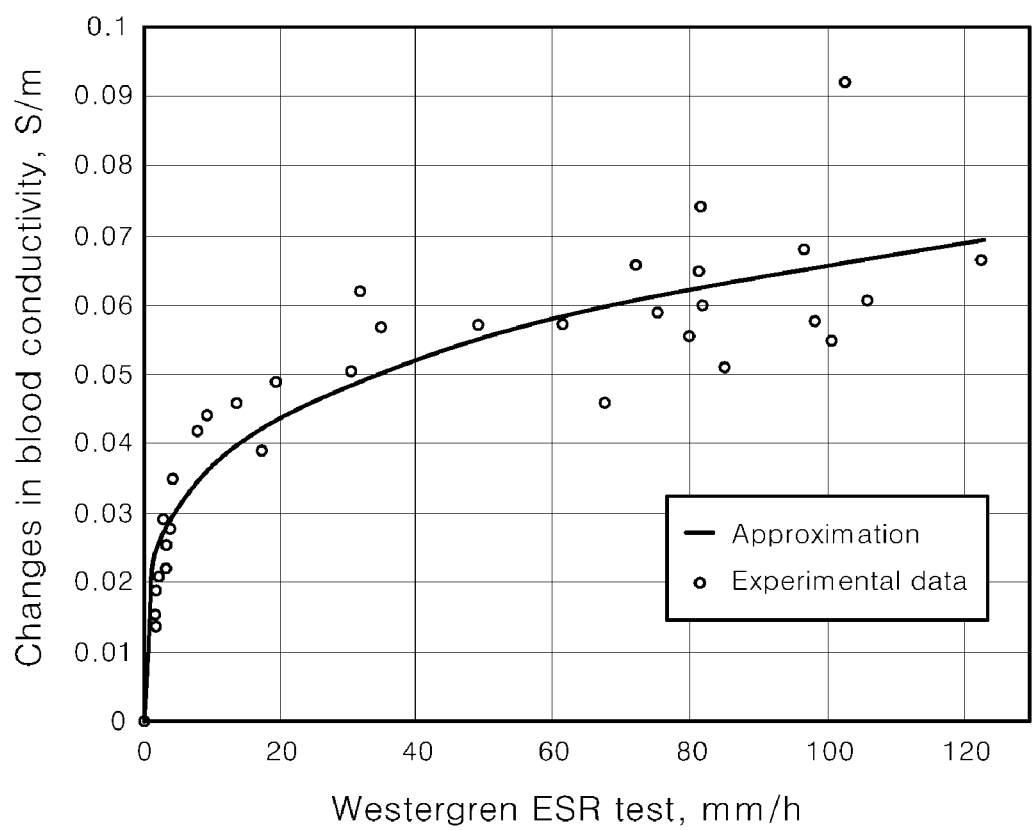
FIG. 3 is a graph showing correlation between changes in blood conductivity measured according to one embodiment of the invention and results of the Westergren ESR test.

FIG. 3 is a graph showing correlation between changes in blood conductivity measured according to one embodiment of the invention and results of the Westergren ESR test.

As shown in FIG. 3, it can be seen that there is evident correlation between changes in blood conductivity measured according to one embodiment of the invention and results of the Westergren ESR test.

In this embodiment, measurement of changes in blood conductivity and the Westergren ESR test were conducted under the following conditions:

As the chamber 101, a rectangular prismatic polydimethylsiloxane (PDMS) chamber having a width of 4 mm and a depth of 5 mm was used, and, as the pair of electrodes 102a, 102b, two gold-plated two-dimensional planar electrodes each having a width of 300 μm and being placed at a distance of 1200 μm from one another were used. A portion of each of the electrodes brought into contact with blood had a length of 4 mm. The planar electrodes were fabricated by a typical lithography process.

As the conductivity meter 104, an impedance analyzer (HIOKI IM3570, HIOKI, Corp.) was used. Blood samples were introduced into the chamber 101 using a pipette. Each sample was tested three times using the same equipment. Here, resistance of the blood samples depends on the geometrical area of the chamber and the electrodes. A KCl standard solution having a known conductivity value was used to calibrate the equipment. Through calibration, the measured resistance values were converted into respective conductivity values.

Although some embodiments have been described with reference to the drawings, it should be understood that the present invention is not limited to these embodiments, and that various modifications, changes, and alterations can be made without departing from the spirit and scope of the invention. Therefore, the scope of the invention should be limited only by the accompanying claims and equivalents thereof.

What is claimed is:

1. A method for measuring an erythrocyte sedimentation rate based on a change in conductivity of blood over time, comprising:
    introducing blood into a chamber; and
    measuring conductivity of the blood using a pair of electrodes,
    wherein the change in conductivity is found based on a difference between conductivities measured at two points of time,
    wherein the two points of time are selected from a time section after the conductivity starts to decrease,
    wherein the erythrocyte sedimentation rate is measured through comparison of the change in conductivity with an erythrocyte sedimentation rate measured by the Westergren method, and
    wherein a relationship between the change in conductivity and the erythrocyte sedimentation rate measured by the Westergren method is represented by the following equation:

$$\Delta\sigma = \lambda W^\gamma$$

where $\Delta\sigma$ denotes a difference (unit: S/m) between conductivities of the blood measured at predetermined points of time, denotes an erythrocyte sedimentation rate (unit: mm/h) measured by the Westergren method, and $\lambda$ and $\gamma$ denote fitting parameters, wherein the fitting parameters are calculated by regression analysis.

2. The method according to claim 1, wherein the pair of electrodes is placed in a bottom surface of the chamber.

3. A method for measuring an erythrocyte sedimentation rate based on a change in conductivity of blood over time, comprising:
    introducing blood into a chamber; and
    measuring conductivity of the blood using a pair of electrodes,
    wherein the change in conductivity is found based on a difference between conductivities measured at two points of time,
    wherein the two points of time are selected from a time section after the conductivity starts to decrease,
    wherein the erythrocyte sedimentation rate is measured through comparison of the change in conductivity with an erythrocyte sedimentation rate measured by the Westergren method, and
    wherein a relationship between the change in conductivity and the erythrocyte sedimentation rate measured by the Westergren method is represented by the following equation:

$$\Delta\sigma = \lambda \log(1+W)$$

where $\Delta\sigma$ denotes a difference (unit: S/m) between conductivities of the blood measured at predetermined points of time, and $\lambda$ denotes an erythrocyte sedimentation rate (unit: mm/h) measured by the Westergren method, and denotes fitting parameters, wherein the fitting parameters are calculated by regression analysis.

4. The method according to claim 3, wherein the pair of electrodes is placed in a bottom surface of the chamber.

5. A method for measuring an erythrocyte sedimentation rate based on a change in conductivity of blood over time, comprising:
   introducing blood into a chamber; and
   measuring conductivity of the blood using a pair of electrodes,
   wherein the change in conductivity is found based on a difference between conductivities measured at two points of time,
   wherein the two points of time are selected from a time section after the conductivity starts to decrease,
   wherein the erythrocyte sedimentation rate is measured through comparison of the change in conductivity with an erythrocyte sedimentation rate measured by the Westergren method, and
   wherein a relationship between the change in conductivity and the erythrocyte sedimentation rate measured by the Westergren method is represented by the following equation:

$$\Delta\sigma = \lambda \frac{W}{W+\gamma}$$

where $\Delta\sigma$ denotes a difference (unit: S/m) between conductivities of the blood measured at predetermined points of time, denotes an erythrocyte sedimentation rate (unit: mm/h) measured by the Westergren method, and $\lambda$ and $\gamma$ denote fitting parameters, wherein the fitting parameters are calculated by regression analysis.

6. The method according to claim 5, wherein the pair of electrodes is placed in a bottom surface of the chamber.

7. A method for measuring an erythrocyte sedimentation rate based on a change in conductivity of blood over time, comprising:
   introducing blood into a chamber; and
   measuring conductivity of the blood using a pair of electrodes,
   wherein the change in conductivity is found based on a difference between conductivities measured at two points of time,
   wherein the two points of time are selected from a time section after the conductivity starts to decrease,
   wherein the erythrocyte sedimentation rate is measured through comparison of the change in conductivity with an erythrocyte sedimentation rate measured by the Westergren method, and
   wherein a relationship between the change in conductivity and the erythrocyte sedimentation rate measured by the Westergren method is represented by the following equation:

$$\Delta\sigma = \lambda \left[ \left(\frac{1}{\gamma}\right)^2 - \left(\frac{1}{W+\gamma}\right)^2 \right]$$

where $\Delta\sigma$ denotes a difference (unit: S/m) between conductivities of the blood measured at predetermined points of time, W denotes an erythrocyte sedimentation rate (unit: mm/h) measured by the Westergren method, and $\lambda$ and $\gamma$ denote fitting parameters, wherein the fitting parameters are calculated by regression analysis.

8. The method according to claim 7, wherein the pair of electrodes is placed in a bottom surface of the chamber.

* * * * *